United States Patent
Padmanabhan et al.

(10) Patent No.: US 6,794,981 B2
(45) Date of Patent: Sep. 21, 2004

(54) INTEGRATABLE-FLUID FLOW AND PROPERTY MICROSENSOR ASSEMBLY

(75) Inventors: Aravind Padmanabhan, Plymouth, MN (US); Jay G. Schwichtenberg, New Hope, MN (US); Cleopatra Cabuz, Edina, MN (US); Ernest Satren, Bloomington, MN (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 10/150,851

(22) Filed: May 16, 2002

(65) Prior Publication Data

US 2002/0190839 A1 Dec. 19, 2002

Related U.S. Application Data

(63) Continuation-in-part of application No. 09/656,694, filed on Sep. 7, 2000, which is a continuation-in-part of application No. 09/207,165, filed on Dec. 7, 1998, now Pat. No. 6,184,773, and a continuation-in-part of application No. 09/368,621, filed on Aug. 5, 1999, now Pat. No. 6,322,247, which is a continuation-in-part of application No. 09/239,125, filed on Jan. 28, 1999, now Pat. No. 6,361,206.

(51) Int. Cl.$^7$ ................................................. H01C 3/04
(52) U.S. Cl. ........................ 338/25; 338/13; 73/204.25
(58) Field of Search .................... 338/25, 13; 73/204.25

(56) References Cited

U.S. PATENT DOCUMENTS

| | | |
|---|---|---|
| 3,680,028 A | 7/1972 | Black et al. |
| 4,085,398 A | 4/1978 | Bertram et al. |
| 4,400,684 A | 8/1983 | Kushida et al. |
| 4,542,650 A * | 9/1985 | Renken et al. ................. 73/196 |
| 4,685,331 A | 8/1987 | Renken et al. |
| 4,703,555 A | 11/1987 | Hubner |
| 4,722,609 A | 2/1988 | Epstein et al. |
| 4,972,708 A | 11/1990 | Wiegleb et al. |
| 5,056,362 A | 10/1991 | Ang et al. |
| 5,057,811 A | 10/1991 | Strott et al. |
| 5,353,638 A | 10/1994 | Marek |
| 5,384,267 A * | 1/1995 | Hutchins et al. ............... 438/59 |
| 5,430,428 A | 7/1995 | Gerblinger et al. |
| 5,473,304 A | 12/1995 | Friese et al. |
| 5,550,526 A | 8/1996 | Mottahed |
| 5,798,684 A | 8/1998 | Endo et al. |
| 5,869,749 A * | 2/1999 | Bonne et al. ............... 73/53.01 |
| 6,032,527 A | 3/2000 | Genova et al. |
| 6,382,228 B1 | 5/2002 | Cabuz et al. |

* cited by examiner

Primary Examiner—Karl D. Easthom
(74) Attorney, Agent, or Firm—Kris T. Fredrick

(57) ABSTRACT

An integratable fluid flow and property microsensor assembly is configured to be operably embedded in a microfluidic cartridge of the type used in lab-on-a-chip systems. The assembly is a robust package having a microstructure flow sensor contained within a housing in order to achieve a robust sensing device. The cartridge provides a flow path to the assembly, which directs the fluid across the flow sensor and returns the fluid to the cartridge flow path. The flow sensor monitors the controlled flow of fluid and transmits signals indicative of that flow. The assembly structure provides a robust sensor that is operable and accurate in many different applications.

12 Claims, 6 Drawing Sheets

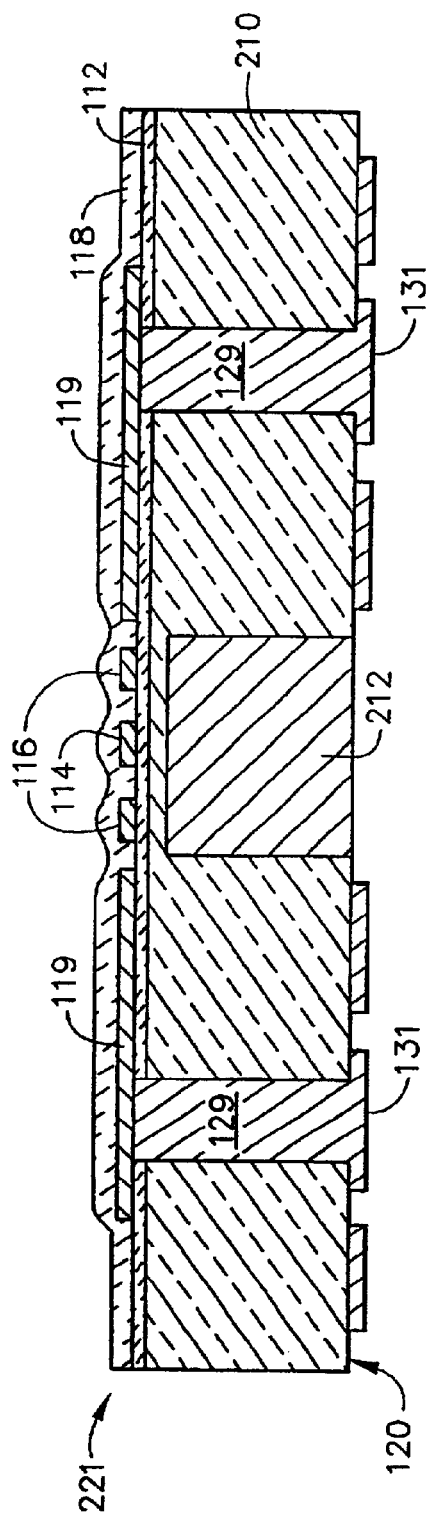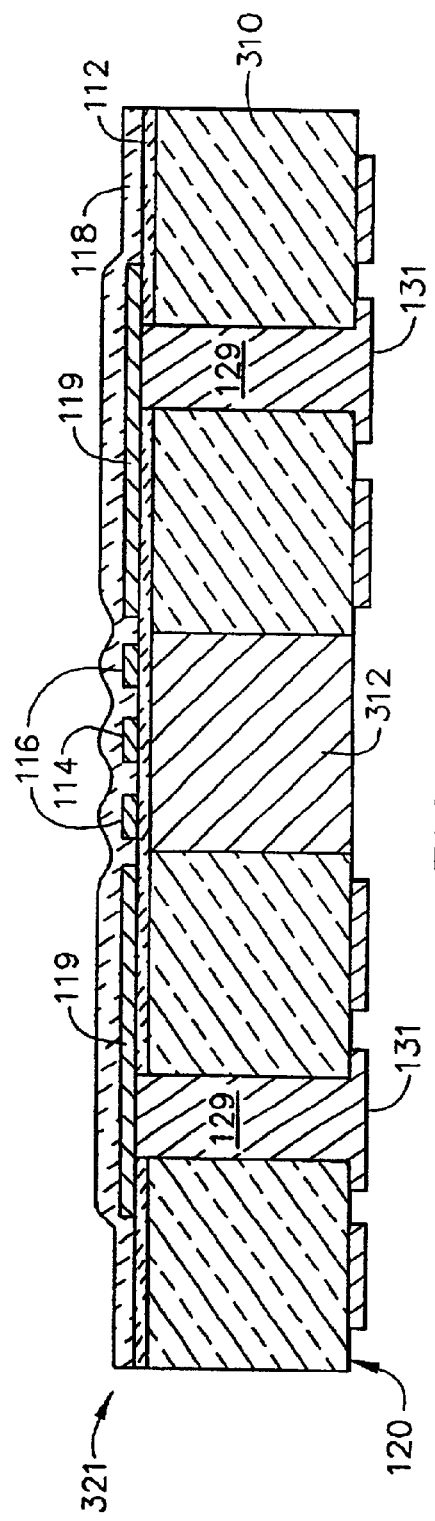

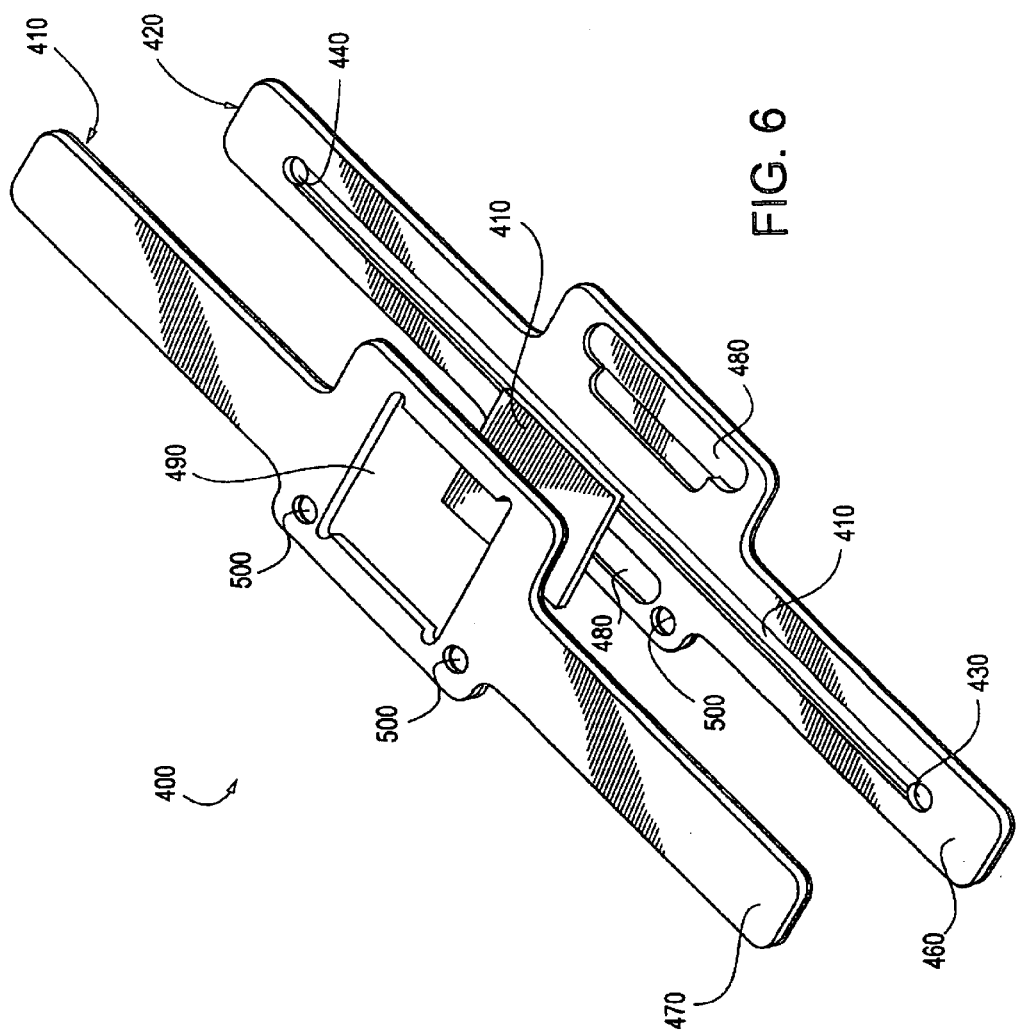

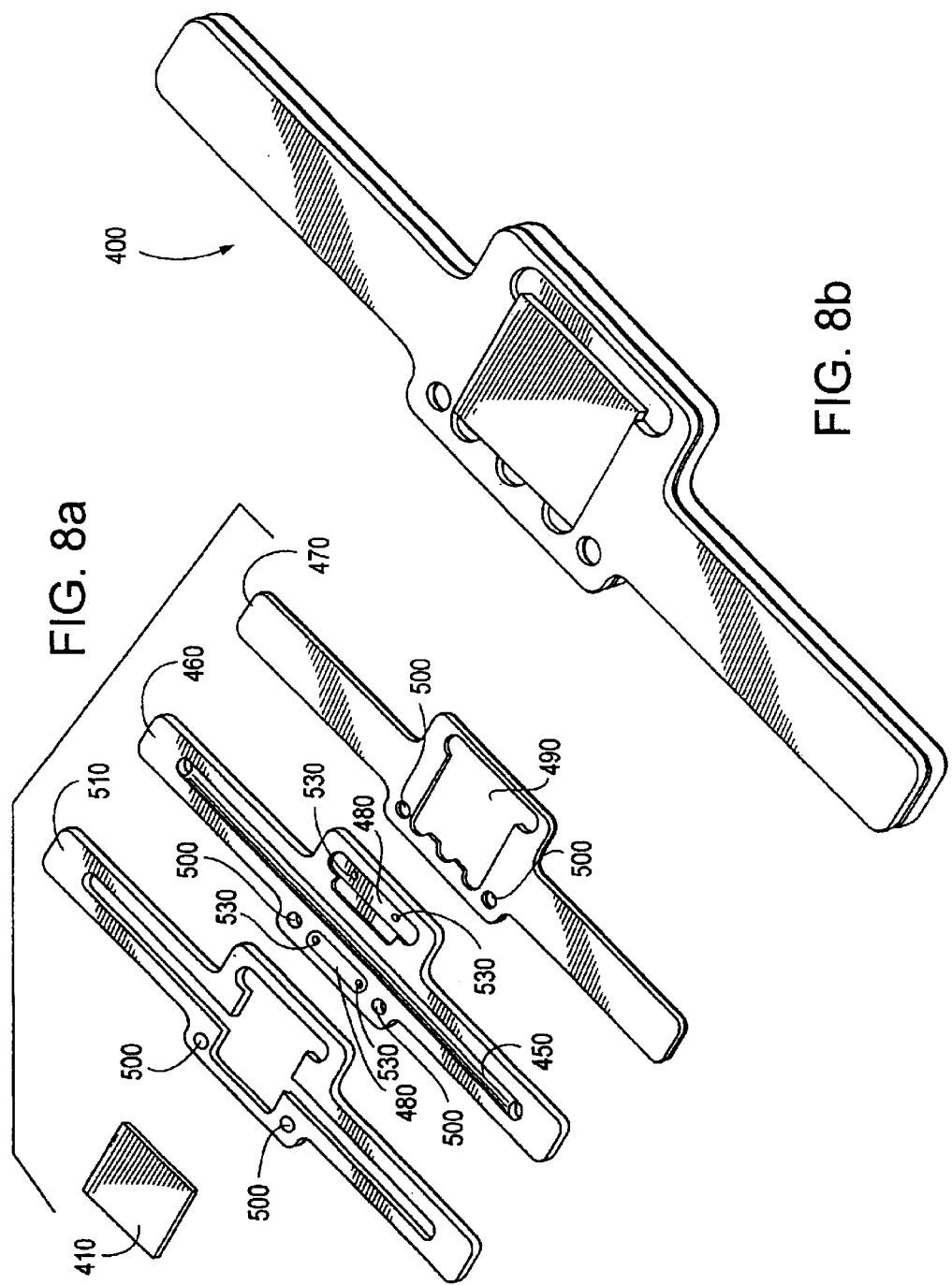

INTEGRATABLE-FLUID FLOW AND PROPERTY MICROSENSOR ASSEMBLY

This is a continuation in part of U.S. patent application Ser. No. 09/656,694 filed Sep. 7, 2000, entitled "Robust fluid and Property Microsensor Made of Optimal Material," which is a continuation-in-part of U.S. patent application Ser. No. 09/207,165, filed Dec. 7, 1998, entitled "Rugged Fluid Flow and Property Microsensor," now U.S. Pat. No. 6,184,773, and U.S. patent application Ser. No. 09/368,621, filed Aug. 5, 1999 now U.S. Pat. No. 6,322,247, which is a Continuation-in-Part of U.S. patent application Ser. No. 09/239,125, filed Jan. 28, 1999, now U.S. Pat. No. 6,361,206 both entitled "Microsensor Housing".

BACKGROUND OF THE INVENTION

1. Field of the Invention

The present invention relates generally to thermal sensors of fluids, such as fluid flow sensors incorporated into a robust package in microstructure form. For convenience sake the term "flow sensor" will be used generically hereinafter for such thermal sensors. The reader will appreciate that such sensors may be utilized to measure primary properties such as mass flow rate, temperature, thermal conductivity and specific heat; and that the heat transfers may be generated through forced or natural convection. The invention relates specifically to a cartridge or assembly which exploits the capabilities of a microstructure flow sensor. Even more specifically, a sensor of the Microbrick™ or microfill type is utilized having a central heating element and surrounding sensor arrays which are structurally robust and capable of operating in harsh environments. These Microbrick™ or microfill sensors include through-the-wafer interconnects thus providing very low susceptibility to environmental damage or contamination. The material of the sensor support structure is of thermal conductivity tailored to the application thus producing a more useful and versatile sensor, such as needed for high sensitivity or high mass flux fluid flow measurement or measurements in harsh environments.

2. Description of Related Art

Open microbridge structures such as detailed in U.S. Pat. 5,401,155, to Higashi et al., are well suited for measurements of clean gases, with or without large pressure fluctuations, since the microbridge structure is burst-proof. However, due to the open nature of the microbridge structure, condensates from vapor can be uncontrollably retained in the microbridge structure leading to uncontrolled changes in its thermal response, or output, making the structure susceptible to output error and poor stability.

The typical microbridge structure has a silicon die wire bonded at the top surface to a header, or substrate, carrying further electrical leads and/or electronics. Typically, such wire for the wire bonds would be a one mil gold wire. This wire has a tendency to retain particles suspended in the fluid, retain liquid condensates, increase undesirable turbulence, and shift flow response. Due to its thinness, the wire is also susceptible to damage in a high mass flux environment, such as high rate liquid flow, and upon attempts to clean the sensor.

Membrane-based sensors overcome some of the problems of the microbridge structure because there is no opening exposed to the fluid. More specifically, there is no opening allowing the fluid to enter the underlying structure. However, because the membrane is sealed over an isolation air space and subject to differential pressure induced stress signal errors, membrane based sensors have limited application in high pressure applications. Due to the physical configuration of the membrane, it can deform or burst as pressure differences (on either side of the membrane) increase above 100 PSI (pressure levels that are very possible in high mass flux environments). The heating/sensing elements on the top surface of the membrane sensors are also typically wire bonded to other components, leaving the problems of the wire in the flow path accumulating debris and possibly breaking during cleaning attempts.

While many different materials may be used to make a fluid flow sensor, the choice of material can drastically affect the sensor's performance. A preferable material making up the sensor substrate would have a relatively low thermal conductivity among other characteristics. This low thermal conductivity is necessary to maintain the sensitivity for the sensor. With this relatively low thermal conductivity, all heating/cooling effects presented to the various sensing elements are caused predominatly by the fluid to be sensed. Stated alternatively, it is important to ensure that heat is not transmitted through the substrate excessively, resulting in signal shorts.

The micromembrane structure discussed above provides a design approach that enables accurate thermal measurements to be made in harsh environments (condensing vapors, with suspended particles, etc.). Specifically, the mass of silicon immediately below the heater/sensing elements is greatly reduced or eliminated, thus limiting potential heat losses. Even in this structure, however, the selection of materials is critical—low thermal conductivity and appropriate material strength continue to be very important. A disadvantage of this structure is its sensitivity to differential pressure (across its membrane) which induces a stress in the sensing elements and results in uncontrolled output signal changes or errors.

In addition to the above referenced thermal characteristics, it is highly desirable for the overall flow sensor to be chemically inert, corrosion resistant, highly temperature stable, electrically isolated, and bio-compatible. Obviously, many of these characteristics are achieved by proper selection of materials. Further, these desired characteristics are necessary in light of the sensors' operating environment. The materials chosen must provide for a sensor which is capable of operating in harsh environments.

It would therefore be desirable to develop a flow sensor which is not susceptible to the above referenced problems. Specifically, the sensor would not be affected by vapor accumulation beneath the microbridge, and would not have exposed bonding wire near the heating and sensing elements. The desirable sensor would be structurally robust and thus capable of operating in harsh environments. Further, it would be desirable to develop a flow sensor which is not affected by signal shorts, thus capable of sensing high mass airflows and liquid flows. To accomplish this a desired flow sensor would include a robust substrate or die with relatively low thermal conductivity, high temperature stability, high electrical isolation, corrosion resistance, chemical inertness, and biocompatability. The design of such a structure would enable flow rate and thermal property sensing over wide ranges at high pressure. Further, this capability would provide trouble free operation in hostile environments. The desirable flow sensor and associated housing would also minimize dead volume and promote cost-efficiency, portability, and miniaturization. The sensor would also be adaptable to monitor the flow through a predetermined flow channel attached to the sensor.

SUMMARY OF THE INVENTION

The present invention details a microstructure flow sensor having a microsensor die with a Microbrick™ or microfill structure (each having a substantially solid structure beneath the sensing elements) and through-the-wafer electrical interconnections. This structure provides a robust sensor that is operable and accurate in many different applications, including harsh environments.

Additionally, the microstructure flow sensor may be incorporated into an assembly in order to achieve a robust sensing device. The assembly is a robust package, configurable so that it may be operably integrated into a microfluidic cartridge of the type used in lab-on-a-chip systems. The flow sensor in the assembly monitors the controlled flow of fluid in the cartridge and transmits signals though flex circuits indicative of that flow. The integration of the assembly and the cartridge yields the benefits of larger instruments through a smaller device.

The sensor features a flat, passivated, top surface overlying the heater and sensor elements to provide appropriate electrical isolation. Further, a die with through-the-wafer interconnections eliminates the need for bonding wires with their attendant problems as discussed above. In order to withstand a wide range of pressure levels and operate in harsh environments, the die structure is configured to be very robust. The die is made up of materials that have very low thermal conductivity, thus eliminating the possibility of undesired thermal signal shorts. For example, the die may be fabricated using various glass materials, alumina, or combinations of such materials.

The die is attached to a substrate having a suitably matched coefficient of thermal expansion (CTE) by any number of adhesives. Electrical contact is made by thermocompression bonding, solder bumping, conductive adhesives or the like. Preferably the through-the-substrate electrical contacts terminate in the necessary electrically conductive runs for attachment to further electronics of the sensor. This allows for easy interconnection to further devices as described below.

The substrate may further have a passivation layer at the mating surface with the die in order to provide a fluid barrier to the bottom of the die and back fill seals to prevent access to the back-side contacts. Both silicon oxide and silicon nitride layers may be used in the construction of the die. The present invention will benefit the user by trouble free and reliable service in all fluid flow applications as well as being easily fabricated and easily subjected to cleaning maintenance.

The ability to perform high mass flux sensing operations is largely dependent upon the physical characteristics of the sensor. Most importantly, low thermal conductivity of the die substrate is necessary in order to create a sensor capable of operating in these high mass flux sensing situations. By minimizing the thermal conductivity, interference with sensor heating/cooling effects will be minimized and the sensing capabilities are enhanced. Specifically, the characteristics of the die substrate materials will control the proper route of heat transfer, avoiding transfer through the die substrate from the heater to the sensors. Various materials can provide this characteristic. Historically, silicon nitride of a microbridge sensor chip has been used to provide certain levels of thermal conductivity, while also being easily manufactured. However, its fragility prevents is use in harsh environments.

A more optimum material which exhibits the desired characteristic is glass. Glass, however, has not been previously used because it has not been easily micromachined. That is, it is difficult to form the required structures using glass. Another potential substrate material is alumina, which is widely used for electronics packaging and can be machined to serve as substrate with some desirable characteristics. One undesirable feature, however, is its high thermal conductivity, which would severely reduce the sensitivity of the sensor chip.

Recent developments in glass materials, including photosensitive glass and pyrex, have shown that micromachining is possible and extremely effective. Consequently, this material can now provide an alternate die substrate for a micromachined flow and property sensor. The present invention exploits the characteristics of glass (photosensitive glass, fused silica, etc.) or alumina materials to produce a flow and property sensor with optimized physical characteristics. Providing a glass based sensor in a Microbrick™ or microfill structure consequently enables the fabrication of a rugged sensor for sensing liquid properties or high mass flux fluid flow, without pressure-stress-induced error signals.

Due to the recent developments in glass, the use of this material as a die substrate generally reduces the amount of structural machining necessary. More specifically, the substrate can now be fabricated in a Microbrick™ or microfill structure which has a substantially solid structure. In this type of sensor die, the heating and sensing elements are placed directly on the substrate and no further processing or structuring is required beneath those elements. Consequently, the substrate itself is continuous beneath the sensing elements creating a more robust sensor die. The characteristics of the glass substrate material allows this Microbrick™ structure to be effectively used in harsh environments.

Alternatively, the same Microbrick™ structure can be achieved utilizing a plug type configuration. In this approach, a substrate material includes a hole under the heating and sensing elements or opening extending completely therethrough. This hole is then refilled with a filler or plug of appropriate materials creating a microfill structure (i.e. a micro hole filled with solid material). The combination of this substrate and the appropriate filler or plug can effectively tailor the thermal characteristics of the microsensor die. For example, the substrate may be largely fabricated from alumina, and include a glass plug. The heating elements are then placed directly upon this plug element, thus providing the necessary thermal characteristics.

The microstructure flow sensor is configurable such that it may be operably incorporated into a flow sensor assembly in order to achieve a more complete sensing device. Specifically, a flow sensor assembly may include the flow sensor contained within a cooperating sensor housing. The sensor housing defines a sealed flow channel, which directs fluid across the flow sensor, and provides a fluid inlet and a fluid outlet at either end of the flow channel. The sensor die meters the volume of reagents and other fluids flowing through the sealed flow channel. As the configuration of the sealed flow channel is known, this operates as a metering flow channel.

The sensor housing may include two layers; a channeled layer and a cover layer. A precision groove in the channeled layer defines the flow channel, a portion of which is enclosed by the attachment of the cover layer to the channeled layer. The cover layer further defines a window for exposing the flow sensor to transmit signals other devices. The flow sensor is arranged on the channeled layer such that its sensing surface also encloses the remaining portion of the flow channel, creating a sealed metering flow channel. The channeled layer and the cover layer may be attached through a variety of means, including a process whereby an epoxy layer is provided between the layers creating a seal therebetween. The groove in the channeled layer is created with substantial precision such that the resultant flow channel provides the desired flow control. Further, the flow sensor is received in the channeled layer and aligned such that its sensing surface is substantially arranged to provide precise metering of the reagents and other fluids flowing through the flow channel.

The flow sensor assembly is a versatile and robust package, configurable so that it may be operably embedded on a microfluidic cartridge of the type used in lab-on-a-chip systems. The sensor of the assembly monitors the controlled flow of fluid in the cartridge and includes electrical connectors for transmitting signals indicative of that flow.

For example, the flow sensor assembly may enable a micro-cytometry cartridge, designed for counting and classifying cells, especially blood cells. The cartridge may accept a blood sample, and provide a flow path for the blood cells within the cartridge. The cartridge flow path introduces the blood into the fluid inlet of the sensor assembly and, after metering the blood flow rate across the sensor, receives the cells from fluid outlet. The micro-cytometry cartridge may further implement multiple sensor assemblies, each metering the flow rate of blood and other reagents at distinct points in the cartridge path.

This integrated structure brings the capabilities of larger and costlier instruments to smaller devices and provides many benefits. The reduced size of the sensor assembly and the cartridge promotes cost reduction and minimizes dead volume flow. The small size and light weight design of the sensor and cartridge increase its portability and self-containment advantages. Additionally, a sensor assembly embedded on a cartridge may be reused on another cartridge, thereby sparing the expense of a new sensor after each use and at the same time benefiting from the functionality and capabilities provided by the cartridge. Depending on the nature of the cartridge, however, it may be preferable to dispose of both sensor assembly and the cartridge after use.

BRIEF DESCRIPTION OF THE DRAWINGS

The present invention will be more fully and completely understood from a reading of the Description of the Preferred Embodiment in conjunction with the drawings, in which:

FIG. 4 is a cross sectional drawing of an alternative microsensor die structure incorporating a filler portion;

FIG. 5 is a cross sectional drawing of yet another microsensor die structure using a plug; and FIG. 6 is an exploded illustration of the flow sensor assembly including a flow sensor and flow sensor housing according to the present invention.

FIG. 8a is an illustration of the flow sensor assembly prior to assembly according to the present invention.

FIG. 8b is an illustration of the flow sensor assembly after assembly according to the present invention.

DETAILED DESCRIPTION OF PREFERRED EMBODIMENTS

Figure 1:
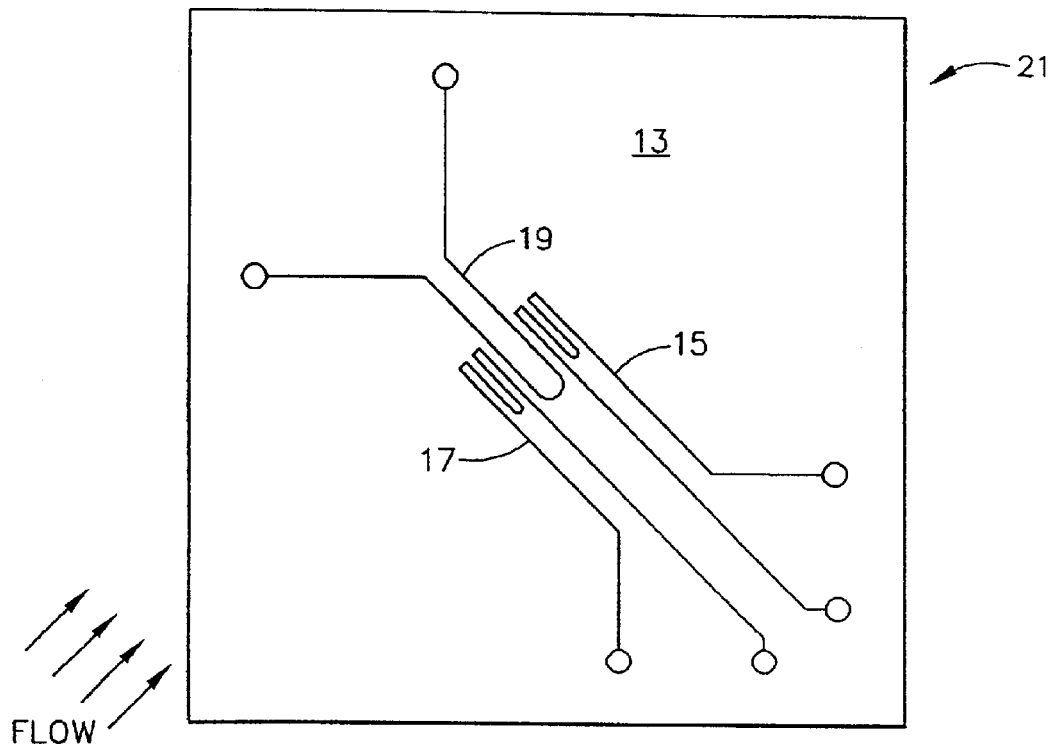
FIG. 1 is a top view of the microsensor die showing the micromembrane heater and sensing elements.

Throughout the Description of the Preferred Embodiment, like components will be identified by like reference numerals.

Referencing FIG. 1, a fluid flow sensor die 21 includes a body 13. Onto body 13 are deposited sensor elements 15, 17 surrounding a central heating element 19; all composed of a suitable metal, such as platinum. The arrangement and theory of operation for a microstructure fluid flow sensor of this type is known to those in the art and will not be further elaborated on herein. Again, for convenience sake, this structure will be generally referred to as a "flow sensor," as indicated above.

Figure 2:
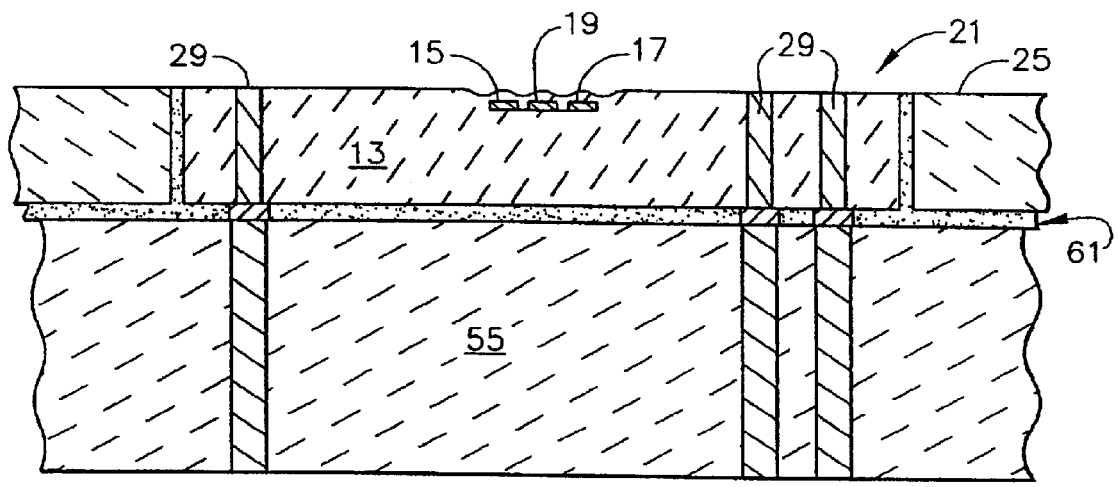
FIG. 2 is a cross section of an assembled fluid flow sensor according to the present invention including a substrate structure.

Referencing FIG. 2, a flow sensor according to the present invention may include a microsensor die 21 bonded to a substrate 23 having a suitably matched coefficient of thermal expansion (CTE). Material for substrate 23 may include alumina, mullite, or known printed circuit board material having suitable CTE. A top surround body, or layer, 25 is placed on the substrate 23 to surround microsensor die 21 in order to further planarize the top surface of the sensing apparatus and provide minimal resistance to fluid flow and minimal crevices into which particles or condensates may lodge. The top surround 25 may be implemented as a epoxy layer, a preform, or any suitably constructed and arranged deposition or structural layer serving the above noted purposes. The joints between substrate 23, die 21, and top surround 25 may be further sealed or smoothed with a suitable epoxy or the like to remove potential dust and vapor traps.

As shown, microsensor die 21 comprises a body 13 having through-holes serving as electrical vias, collectively 29, filled with an electrical conductor material, preferable gold, chrome/gold alloy, or chrome/gold/palladium alloy. The use of through the way for interconnects, such as shown, provides many advantages for the flow sensor. Specifically, no wire bonds are extending upward from the upper surface of microsensor die 21. Consequently, there are no structures which interfere with the flow being sensed. As is expected, this eliminates any turbulence, along with avoiding stresses on the particular bonding structures.

Again, referencing FIG. 2, the substrate 23 comprises a substrate body 55 comprised of alumina, mullite, or other known materials having coefficient of thermal expansion (CTE) suitably matched to the microsensor die 21. At the top surface of the substrate structure 23 which is to be mated with the silicon microsensor die 21 there is located a thermocompression solder-bump bond 51.

Silicon is often considered a very effective microsensor body material because it can be easily machined/processed using several well known silicon processing techniques. In certain applications, such as very high mass flux fluid flow sensing and high pressure applications, such silicon supported structures as microridges or mciromembranes do have certain disadvantages however. Specifically, the thermal isolation characteristics of silicon would limit structural and operational characteristics of a sensor if built directly on silicon. In order to deal with these thermal characteristics, the microsensor body of a silicon based sensor is configured in a micromembrane type structure, so as to limit the thermal mass below the heater and sensing elements. Obviously, this limits the physical strength of a silicon based sensor. In addition, this micromembrane configuration is not suitable for high mass flux sensing because its output signal saturates before reacting high flux levels.

In order to effectively operate in harsh environments, the flow sensor must be structurally robust. As suggested above, the membrane structure, which burst near 100 PSI, does not exhibit the structural characteristics required to create a robust sensor. What is needed is a sensor robust enough to withstand high pressures due to sources (such as high pressure pulses, ultrasonic cleaning, and water hammer). In order to sense high mass flux flow rates, it is also necessary to have a substrate material with a thermal conductivity. If it is too low (as in the case of the membrane) the output signal saturates at moderate fluxes (~1 g/cm$^2$s); but if it is too high the output signal becomes too small. Certain glass materials provide better thermal isolation characteristics (than silicon), thus increasing the sensing capabilities of the above-outlined micromachined flow and property sensor. The use of glass also allows for a more robust physical structure to be used. Additionally, the sensing elements will be protected by a passivation layer, thus reducing their sensitivity to vapors and liquids. These various characteristics result in a more versatile sensor which can be used in multiple applications. Furthermore, as outlined below, certain techniques provide for effective micromachining of glass based substrates.

Figure 3:
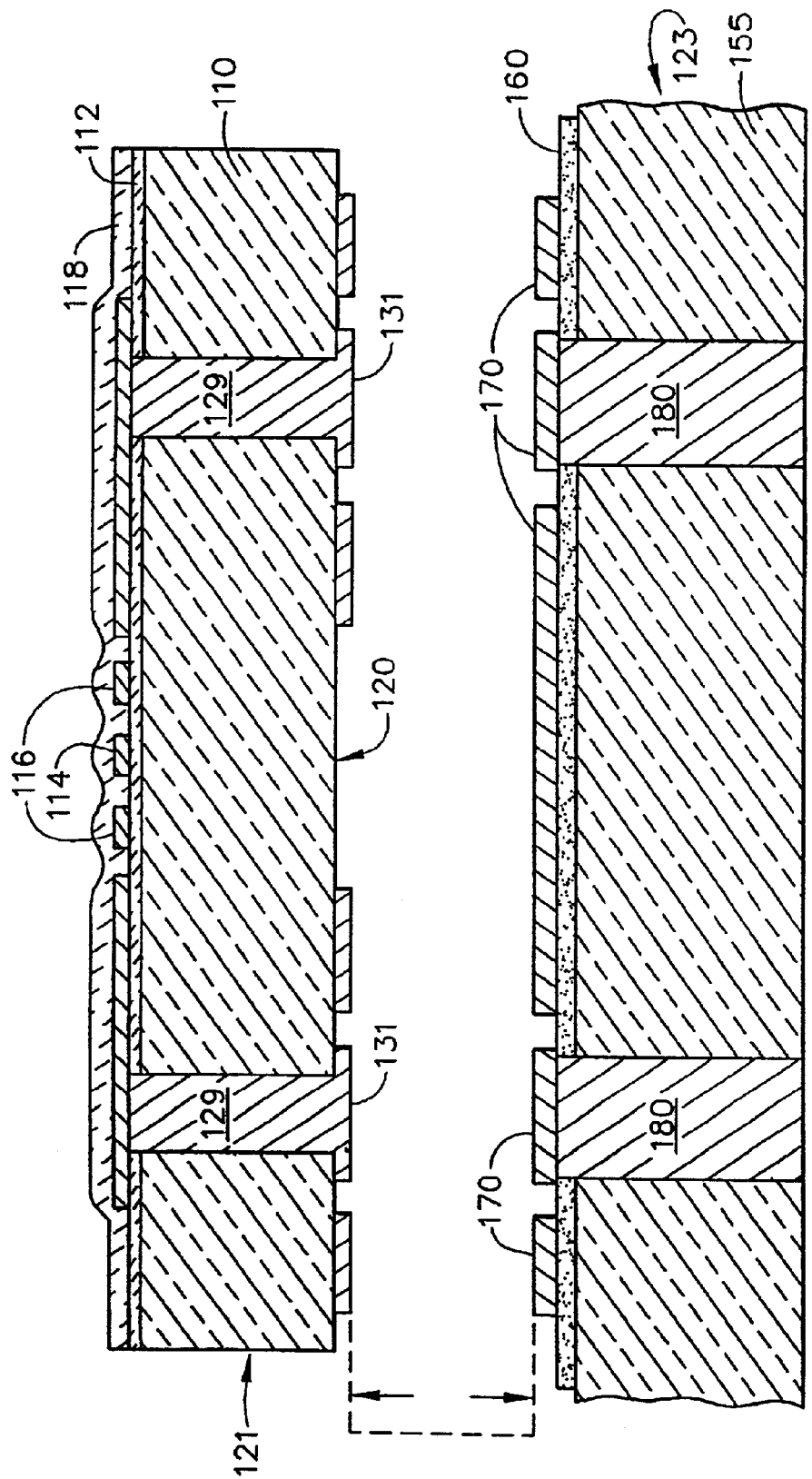
FIG. 3 is a more detailed view of the microsensor die and a substrate.

Referring now to FIG. 3, there is shown a more detailed structure for a glass based air flow or fluid flow sensor. The use of glass as a microsensor body material provides multiple features which enhance the capabilities of the sensor. These features include (1) the automatic electrical insulation for through-the-wafer contacts, (2) lower thermal conductivity than silicon, (3) environmental ruggedness needed to withstand pressure pulses as for sensing liquids, and (5) the ability to use a structurally robust sensor body configuration. Furthermore, the glass based sensor meets all requirements for chemical inertness, corrosion resistance, and biocompatability.

As mentioned above, glass provides inherent electrical isolation between various contacts. This is compared with a silicon based sensor where electrical isolation must be achieved by incorporating silicon dioxide layers on the substrate unless more costly silicon wafers are used that a grown to be slightly insulating. Obviously, this eliminates one layer of material and one necessary processing step. This is particularly beneficial as the step of growing oxide is time consuming and done at fairly high temperatures.

Referring now to FIG. 3, there is shown a cross sectional view of the glass based sensor die 121 of the present invention. While the sensor of the present invention is generally referred to as a glass based sensor, it is understood that other materials having appropriate physical characteristics could also be used. For example, alumina, when appropriately structured, could be used as the base material for forming the sensor die 121. The other materials are intended to be within the scope and spirit of the present invention. A glass body 110 is used as the basis for forming sensor die 121. Upon the upper surface of glass body 110 is a layer of silicon nitride ($Si_xN_y$) 112 which again serves passivation and structural functions. Upon this passivation layer 112 there is constructed the heater element 114 and sensors 116, similar to those described above and well known by those skilled in the art. Once again, these heating and sensing elements can be fabricated from many materials, such as platinum. Covering the entire upper surface of the structure is a top layer 118 which serves as a protective passivation coating. Top layer 118 again is typically silicon nitride ($Si_xN_y$).

Similar to the sensor described above, glass body 110 has a plurality of electrical vias 129 extending therethrough. These electrical vias are typically holes that are created in glass body 110 and provide innerconnection to the backside 120 thereof. Again, this allows electrical connection to further elements of the sensing system. Fabrication of these electrical vias 129 is more fully explained with reference to FIG. 4 below.

Placed within electrical vias 129 is a electrically conductive connecting material 131, which provides electrical connection to the actual heater 114 or sensor 116. The material used for these electrical connections is chosen to closely match the thermal expansion characteristics of glass body 110.

Once again, a substrate 123 is configured for attachment to the backside of microsensor die 121. Substrate 123 includes a substrate main body 155 made up of a material chosen to closely match the thermal characteristics of glass substrate 110. As an example, substrate 123 may be kovar-seal glass, alumina, PCB, etc. Upon the top surface of substrate body 155 is a glazing layer 160 along with a plurality of metal contacts 170. Various through holes or vias 180 can also be provided in substrate body 155 to provide appropriate electrical connection to further components.

In order to provide a operational sensor, sensor die 121 is attached to substrate 123 such that all appropriate electrical connections are properly aligned. This attachment can easily be achieved through thermal compression, or other appropriate attachment mechanisms much as solder bumping or z-axis adhesives.

As can be seen, glass body 110 is a substantially solid block of material. That is, other than the existing electrical vias 129 that are provided for electrical interconnection to components attached to the sensor die 121, there are no other openings or holes therein. Most significantly, the area of glass body 110 directly below heater 114 and sensing elements 116 is substantially solid. As can be expected, this provides an extremely easy structure to fabricate and minimizes the required processing steps. This type of structure can effectively be used due to the nature of the material chosen for body 110. More specifically, by utilizing a glass based material, having low thermal conductivity, an operational fluid flow sensor can be fabricated. This type of structure, commonly referred to as a Microbrick™, provides for a very robust and environmentally sound sensor. Most importantly, this sensor is able to withstand high pressure levels without bursting.

As mentioned above, the use of appropriate materials for glass body 110 makes the Microbrick™ structure possible. Generally speaking, this structure does not work well when silicon is used as the substrate material, due to its high thermal conductivity. Consequently in silicon, a heat transmission path is too easily created through the substrate material itself, resulting in unusually low/signal outputs. As mentioned above, this is highly undesirable for any fluid flow sensing as it diminishes the sensitivity of sensing elements 116 relative to heater 114.

Referring now to FIG. 4, there is shown an alternative embodiment of the present invention. In this modified-micromembrane configuration, a microsensor die 221 is again based upon a glass body 210. As in the embodiment shown in FIG. 3, a passivation layer 112 is deposited immediately upon the upper surface of glass body 210. Upon this passivation layer is fabricated a heater 114 and a pair of sensing elements 116. Also included are top surface interconnections 119 which provide electrical interconnects between the sensing elements and all other appropriate components. Coated on top of these elements (heater 114, sensing elements 116 and interconnections 119) is a protective layer 118.

As can be seen, glass body 210 includes a central filler portion 212 below heater 114 and sensing elements 116. In this embodiment, filler portion 212 further enhances the operation of microsensor die 221 by providing additional thermal isolation between heater 114 and sensing elements 116. As mentioned above, the glass material chosen for glass body 210 provides many advantages and more optimal thermal isolation than silicon. However, glass does have some thermal conductivity characteristics, as do virtually all materials. The transit heating affects, as described above, are further reduced by utilizing a material in filler portion 212 which has thermal conductivity properties even better than glass. Consequently, the overall structure immediately adjacent heater 115 and sensing elements 115 has a very low thermal conductivity characteristic. Consequently, the sensitivity of the sensor at high mass flux fluid flow conditions is greatly enhanced.

Referring now to FIG. 5, there is shown yet another configuration for a microsensor die 321. In this particular configuration, microsensor die 321 is based upon body 310 which is configured somewhat similarly to glass body 210 shown in FIG. 5. However, in this instance, body 310 may be manufactured out of other materials including both glass or silicon or alumina. In order to further tailor the thermal characteristics of microsensor die 321, an appropriately configured plug 312 is utilized. Plug 312 extends completely or entirely through body 310 and is chosen from a material having desired thermal characteristics. As can be seen, heater 114 and sensing elements 116 are configured directly above plug 312. For example, body 310 may be configured from alumina while plug 312 may be configured of appropriate glass material. In this respect, a solid structure is maintained beneath heater 114 and sensing elements 116, while the thermal characteristics are again closely controlled.

The configuration shown in FIG. 5 is particularly applicable when alumina or silicon is used as the body material. As is well known, alumina can be easily machined and manufactured into appropriate configurations using well known methods. Furthermore, alumina is more chemically inert than even glass or silicon. Consequently, the use of alumina alone has advantages in certain applications. Furthermore, alumina can be used in much higher temperature applications as it is more temperature resistant. As mentioned above, using an appropriate plug material, the necessary thermal conductivity can be achieved resulting in a thermal sensor having the desired operational characteristics. This plug or microfill approach can similarly be used with other materials to appropriately "tune" or tailor the characteristics of the sensor.

Referring now to FIG. 6, there is shown in exploded form a flow sensor assembly 400 according to the present invention. The flow sensor assembly 400 includes a microstructure flow sensor 410 and a flow sensor housing 420 arranged such that the flow sensor 410 is contained within the sensor housing 420. Although the housing of the present invention is generally constructed from a plastic or glass material, it is understood that other materials having the appropriate physical characteristics could also be used. The sensor housing 420 defines a flow inlet 430 and a flow outlet 440, which provide a fluid entrance and exit for the flow sensor housing 420 respectively. The flow sensor housing 420 further provides a sealed flow channel 450, which connects the flow inlet 430 and flow outlet 440, and passes the flow sensor 410.

The flow sensor housing 420 contains two layers; a channeled layer 460 and a cover layer 470. A precision groove in the channeled layer 460 defines the sealed flow channel 450 and is substantially enclosed by the cover layer 470 of the housing. The cover layer 470 defines a housing window 490 that exposes a section of the flow channel 450. The flow sensor 410 is arranged on the channeled layer 460 such that its sensing surface encloses the exposed section of the flow channel 450, thereby sealing the flow channel 450 between the channeled layer 460 and the cover layer 470 and the flow sensor 410. A fluid entering the flow inlet 430 flows through the sealed flow channel 450, passing across the flow sensor 410, and exits the sensor assembly through flow outlet 440. The groove in the channeled layer 460 is created with substantial precision resulting in a channel that provides the desired flow control. The housing window 490 exposes the flow sensor 410 so that the sensor may transmit signals to other devices.

Figure 7:
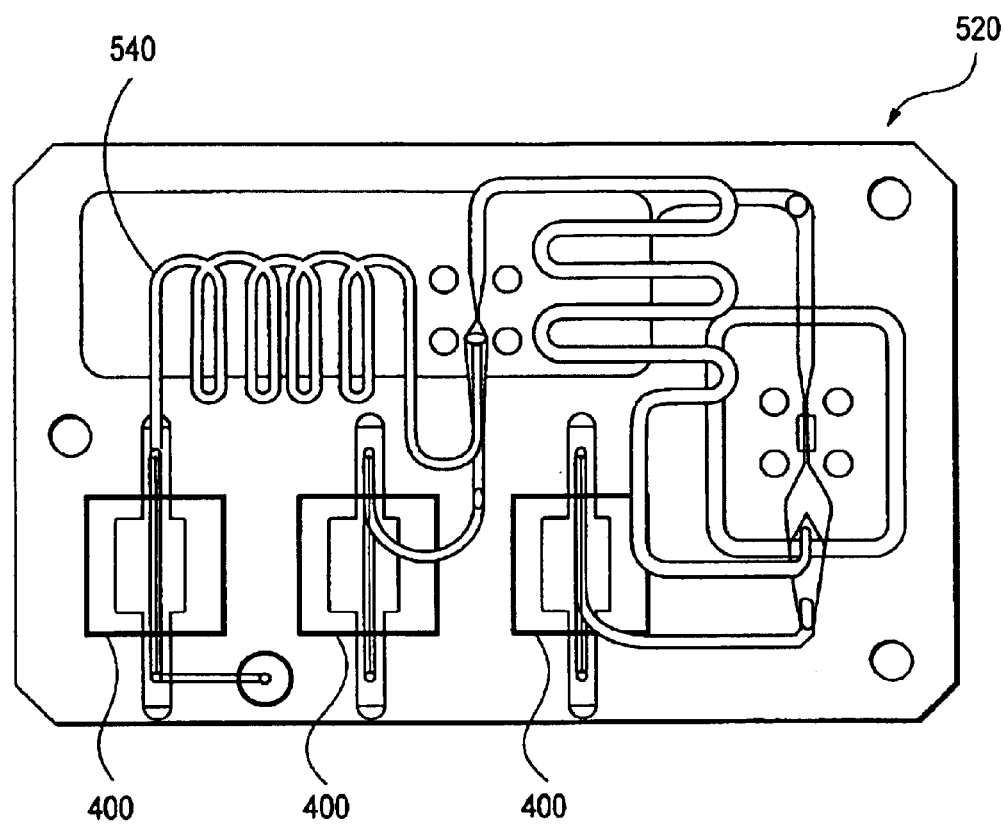
FIG. 7 is an illustration of a microfluidic cartridge with embedded flow sensors according to the present invention.

The flow sensor assembly 400 is a robust package, suitable for operable embedment into other systems, such as a microfluidic cartridge 520 of the type used in lab-on-a-chip systems, as shown in FIG. 7. This integrated structure brings the capabilities of larger and costlier instruments to smaller devices such as the microfulidic cartridge 520. The preferred embodiment of the assembly provides for an assembly width ranging from approximately 3 mm to 6 mm and an assembly length ranging from approximately 6 mm to 25 mm. The flow sensor 410 of the assembly 400 monitors the controlled flow of fluid in the cartridge 520 and includes electrical connectors for transmitting electrical signals indicative of that flow. The electrical connectors may be implemented by flex circuits or ceramic circuit boards, which are known in the art, for providing the electrical signals to the cartridge or other devices. Alternatively, circuit traces directly on the sensor 410 that lead to electrical connections on the cartridge 520 may transmit the electrical signals. Once the electrical signal is transmitted to the edge of the sensor 410, the signal is then propagated to the cartridge 520 or other device by a pogo pin array, card edge connector, or other appropriate means.

Although the embodiment provided for above describes the sensor assembly 400 as a unitary entity that is embedded into a cartridge 520, in an alternative embodiment, the sensor housing 420 is fixedly incorporated into the cartridge while the flow sensor 410 is embedded into the housing 420. In this latter embodiment of the present invention, the housing 420 is a firmly implanted part of the cartridge, and the sensor 410 may be embedded into and removed from the housing 420. This versatile "plug-and-play" type configuration provides for straightforward swapping of flow sensors, in and out of cartridges, while the housing 420 remains part of the cartridge 520. Although not limited by these dimensions, the preferred embodiment of this "plug-and-play" configuration provides for a sensor 410 width ranging from approximately 1.6 mm to 4 mm and a length ranging from approximately 1.6 mm to 5 mm.

In one implementation of the present invention, the flow sensor assembly 400 may be operably embedded in a micro-cytometry cartridge that requires a flow channel meter for metering blood cells. The cartridge 520 may accept a blood sample, and provide a flow path 540 for the blood cells within the cartridge. The cartridge flow path 540 introduces the cells into the flow inlet 430 of the sensor assembly 400 for metering. The blood cells flow through the sealed flow channel 450 across the flow sensor 410 and exit the sensor assembly 400 through the flow outlet 440 back into the cartridge flow path 540. The flow sensor 410 of the assembly 400 monitors the flow of blood cells, and the electrical connectors of the assembly 400 transmit signals indicative of the characteristic of the blood cells being metered. After the micro-cytometry cartridge has been employed, the sensor assembly 400 may be removed for use with another cartridge, while the original cartridge is disposed.

The processing to create the sensor assembly 400 may be accomplished through various methods. One method generally attaches the flow sensor 410 to the cover layer 470 with an epoxy substance, thereby securely seating the flow sensor. The precise seating of the flow sensor 410 ensures that the sensor is received between the two housing layers and aligned such that its sensing surface is substantially arranged for providing precise metering of the reagents and other fluids flowing through the flow channel 450. In order to maintain a precise flow channel 450, which does not encumber or disrupt the fluid flow, the sensor assembly creation ensures that epoxy does not escape into the flow channel 450. As shown in FIGS. 6 and 8*a* sealing recess 480 are formed in the channeled layer 460, for receiving a sealing epoxy as described below. As shown in FIG. 8*a*, multiple epoxy releases 530 are provided in the base of the sealing recesses 480 to discharge excess epoxy and air bubbles in the sealing recesses 480.

Additionally, an epoxy layer 510 is circumscribed with an outside perimeter substantially the same as the channeled layer 460 and the cover layer 470, as shown in FIG. 8*a*. The inside perimeter of the epoxy layer 510 substantially tracks the pattern of the flow channel 450 and the housing window 490, as shown in FIG. 8*a*. Further, the channeled layer 460, the cover layer 470, and the epoxy layer 510 have guide holes 500 therethrough. The guide holes 500 are bored through these layers such that alignment of the holes yields the desired positioning of the cover layer 470 and the epoxy layer 510 with respect to the channeled layer 460.

The abovementioned features of the sensor assembly 400 facilitate a method of creating the assembly. In accordance with this method, the sealing recess 480 are with an epoxy substance such that the substance is substantially flush with the surface of the channeled layer 460, thereby minimizing excess epoxy substance that may otherwise escape into the flow channel 450 and disrupt the desired flow channel form. The channeled layer 460 receives the flow sensor 410, creating a seal therebetween. Excess epoxy and air bubbles in the sealing recess 480 are discharged through the epoxy releases 530. The epoxy layer 510 is aligned with and attached to the channeled layer 460 such that the epoxy layer 510 does not cover the flow channel 450. Using the guide holes 500 for precise positioning, the cover layer 470 and the channeled layer 460 are brought into contact with each other, creating a seal therebetween. The resultant assembly provides a sealed metering flow channel in an assembly designed for embedment on a microfluidic cartridge, shown in FIG. 8*b*.

It will be appreciated by the ordinarily skilled artisan that the present invention offers many advantages and that the detailed structure of the preferred embodiment presents several solutions to a myriad of problems. It will be recognized that various structures of the preferred embodiment may have counterparts substituted therefore when the unique advantages of that particular element are not desired for a selected sensor application. The present invention is thus only to be limited by the appended claims. Having thus described the invention what is claimed is:

What is claimed is:

1. A sensor assembly for monitoring the flow of a fluid which is easily incorporated into a card assembly, the sensor assembly comprising:

a sensor die having a sensing surface which is responsive to the flow of fluid, the sensor die producing a signal indicative of the flow of fluid, the sensor die further having a plurality of electrical contacts for transmitting the electrical signals produced;

a sensor housing containing the sensor die while also providing access to the electrical contacts, the sensor housing having a fluid inlet, a fluid outlet, and a flow channel between the fluid inlet and the fluid outlet, the flow channel configured to direct fluid past the sensing surface, wherein the housing includes a substantially planar channeled portion and a substantially planar cover portion, wherein the flow channel is formed by a groove in the channeled portion which is enclosed by the attachment of the cover portion, and wherein the cover portion includes an opening to receive the sensor die; and a plurality of connectors electrically connected to the electrical contacts for allowing access to the electrical signals by a related system.

2. The sensor assembly of claim 1 wherein the housing is made from a plastic substance.

3. The sensor assembly of claim 1 wherein the housing is made from a glass substance.

4. The sensor assembly of claim 1 wherein the sensor die is attached to both the channeled portion and the cover portion such that the sensing surface further enclosed a portion of the flow channel.

5. The sensor assembly of claim 1 wherein the housing is made from a ceramic substance.

6. The sensor assembly of claim 1 wherein the sensor die produces a signal indicative of a thermal conductivity of the fluid.

7. The sensor assembly of claim 1 wherein the sensor die produces a signal indicative of a specific heat of the fluid.

8. The sensor assembly of claim 1 wherein the plurality of connectors comprises flex circuits.

9. The sensor assembly of claim 1 wherein the plurality of connectors comprises ceramic circuit boards.

10. The sensor assembly of claim 1 wherein the plurality of connectors comprises a plurality of circuit traces on the card assembly for transmitting the electrical signals to an edge of the card assembly.

11. The sensor assembly of claim 10 where the electrical signals are propagated from the edge of the card assembly to the related system via a pogo pin array.

12. The sensor assembly of claim 10 where the electrical signals are propagated from the edge of the card assembly to the related system via a card edge connector.

* * * * *